(12) United States Patent
Chuter et al.

(10) Patent No.: US 8,992,593 B2
(45) Date of Patent: Mar. 31, 2015

(54) APPARATUS AND METHODS FOR DEPLOYMENT OF A MODULAR STENT-GRAFT SYSTEM

(75) Inventors: Timothy A. M. Chuter, San Francisco, CA (US); Blayne A. Roeder, Lafayette, IN (US); Steven J. Charlebois, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 159 days.

(21) Appl. No.: 12/841,807

(22) Filed: Jul. 22, 2010

(65) Prior Publication Data

US 2010/0312326 A1    Dec. 9, 2010

Related U.S. Application Data

(63) Continuation-in-part of application No. 12/332,904, filed on Dec. 11, 2008.

(60) Provisional application No. 61/016,753, filed on Dec. 26, 2007.

(51) Int. Cl.
*A61F 2/06* (2013.01)
*A61F 2/86* (2013.01)
(Continued)

(52) U.S. Cl.
CPC ... *A61F 2/86* (2013.01); *A61F 2/07* (2013.01); *A61F 2/856* (2013.01); *A61F 2/915* (2013.01); *A61F 2002/065* (2013.01); *A61F 2002/828* (2013.01); *A61F 2002/8486* (2013.01); *A61F 2002/91516* (2013.01);
(Continued)

(58) Field of Classification Search
USPC .............. 623/1.13, 1.16, 1.35, 1.27, 23.7
See application file for complete search history.

(56) References Cited

U.S. PATENT DOCUMENTS 5,569,295 A    10/1996    Lam
5,843,164 A    12/1998    Frantzen et al.
(Continued)

FOREIGN PATENT DOCUMENTS

EP          0960607        1/1999
WO    WO 03/082153 A2    10/2003
WO    WO 2008/021556 A1   2/2008

OTHER PUBLICATIONS

Office Action for U.S. Appl. No. 12/622,351 dated Oct. 6, 2010, 12 pgs.
(Continued)

*Primary Examiner* — Paul Prebilic
(74) *Attorney, Agent, or Firm* — Brinks Gilson & Lione

(57) ABSTRACT

The present invention provides a modular stent-graft system. In one embodiment, a prosthesis comprises a first tubular graft comprising a layer of graft material, one lumen extending therein, and a first fenestration extending through the layer of graft material. A layer of fenestration covering material attaches to the layer of graft material. The layer of fenestration covering material is disposed in the lumen of the first tubular graft and partitions the first fenestration from the lumen of the first tubular graft. A first non-stented opening is disposed proximal to the first fenestration and communicates with the first fenestration between the layer of graft material and the fenestration covering material. In use, a proximal end of a second tubular graft sealably engages the first non-stented opening, and the second tubular graft further extends through the first fenestration and into a branch vessel.

6 Claims, 12 Drawing Sheets

(51) Int. Cl.
A61F 2/07 (2013.01)
A61F 2/856 (2013.01)
A61F 2/915 (2013.01)
*A61F 2/82* (2013.01)
*A61F 2/848* (2013.01)
*A61F 2/89* (2013.01)

(52) U.S. Cl.
CPC ............ *A61F 2250/006* (2013.01); *A61F 2/89* (2013.01); *A61F 2002/075* (2013.01); *A61F 2230/0013* (2013.01); *A61F 2230/005* (2013.01); *A61F 2230/0054* (2013.01); *A61F 2230/0067* (2013.01); *A61F 2210/0076* (2013.01); *A61F 2220/0016* (2013.01)
USPC .................... 623/1.13; 623/1.35; 623/1.27

(56) References Cited

U.S. PATENT DOCUMENTS

| | | | |
|---|---|---|---|
| 5,913,897 | A | 6/1999 | Corso et al. |
| 6,071,307 | A | 6/2000 | Rhee et al. |
| 6,348,068 | B1 | 2/2002 | Campbell et al. |
| 6,368,345 | B1 | 4/2002 | Dehdashtian et al. |
| 6,423,090 | B1 | 7/2002 | Hancock |
| 6,582,458 | B1 | 6/2003 | White et al. |
| 6,616,689 | B1 | 9/2003 | Ainsworth et al. |
| 6,629,994 | B2 | 10/2003 | Gomez et al. |
| 6,635,083 | B1 | 10/2003 | Cheng et al. |
| 6,645,242 | B1* | 11/2003 | Quinn .......................... 623/1.16 |
| 6,648,911 | B1 | 11/2003 | Sirhan et al. |
| 7,186,263 | B2 | 3/2007 | Golds et al. |
| 7,341,598 | B2 | 3/2008 | Davidson et al. |
| 7,407,509 | B2 | 8/2008 | Greenberg et al. |
| 7,828,837 | B2* | 11/2010 | Khoury .......................... 623/1.35 |
| 8,394,136 | B2* | 3/2013 | Hartley et al. ............... 623/1.13 |
| 2003/0120263 | A1* | 6/2003 | Ouriel et al. ........................ 606/1 |
| 2003/0130720 | A1 | 7/2003 | DePalma et al. |
| 2003/0199967 | A1* | 10/2003 | Hartley et al. ............... 623/1.13 |
| 2004/0117003 | A1 | 6/2004 | Ouriel et al. |
| 2004/0117004 | A1 | 6/2004 | Osborne et al. |
| 2004/0215316 | A1 | 10/2004 | Smalling |
| 2005/0033406 | A1 | 2/2005 | Barnhart et al. |
| 2005/0049674 | A1 | 3/2005 | Berra et al. |
| 2005/0131516 | A1 | 6/2005 | Greenhalgh |
| 2005/0154446 | A1 | 7/2005 | Phillips et al. |
| 2005/0222671 | A1 | 10/2005 | Schaeffer et al. |
| 2005/0273155 | A1 | 12/2005 | Bahler et al. |
| 2006/0052860 | A1 | 3/2006 | Gomez et al. |
| 2006/0100695 | A1 | 5/2006 | Peacock, III et al. |
| 2006/0184228 | A1* | 8/2006 | Khoury .......................... 623/1.13 |
| 2006/0190075 | A1 | 8/2006 | Jordan et al. |
| 2006/0247761 | A1* | 11/2006 | Greenberg et al. .......... 623/1.16 |
| 2007/0027525 | A1 | 2/2007 | Ben-Muvhar |
| 2007/0168019 | A1 | 7/2007 | Amplatz et al. |
| 2007/0179592 | A1 | 8/2007 | Schaeffer |
| 2007/0203566 | A1 | 8/2007 | Arbefeuille et al. |
| 2007/0208256 | A1 | 9/2007 | Marilla |
| 2007/0225797 | A1 | 9/2007 | Krivoruhko |
| 2007/0233220 | A1 | 10/2007 | Greenan |
| 2007/0244547 | A1 | 10/2007 | Greenan |
| 2007/0250152 | A1 | 10/2007 | Xiao et al. |
| 2008/0109066 | A1* | 5/2008 | Quinn .......................... 623/1.13 |
| 2008/0119943 | A1 | 5/2008 | Armstrong et al. |
| 2008/0269866 | A1* | 10/2008 | Hamer et al. ................. 623/1.11 |
| 2008/0281399 | A1 | 11/2008 | Hartley et al. |
| 2009/0043376 | A1 | 2/2009 | Hamer et al. |
| 2009/0048663 | A1* | 2/2009 | Greenberg .................... 623/1.35 |
| 2009/0105809 | A1 | 4/2009 | Lee et al. |
| 2009/0171437 | A1 | 7/2009 | Brocker et al. .............. 623/1.13 |
| 2012/0323307 | A1* | 12/2012 | Richter ......................... 623/1.16 |

OTHER PUBLICATIONS

Response to Office Action for U.S. Appl. No. 12/622,351 filed Mar. 9, 2011, 15 pgs.
Office Action for U.S. Appl. No. 12/332,904 dated Oct. 4, 2010, 10 pgs.
Response to Office Action for U.S. Appl. No. 12/332,904 filed Mar. 4, 2011, 13 pgs.
Office Action for U.S. Appl. No. 12/472,082 dated Oct. 4, 2010, 10 pgs.
Response to Office Action for U.S. Appl. No. 12/472,082 filed Mar. 4, 2011, 14 pgs.
European Search Report for corresponding EP 11174880 dated Jul. 23, 2012 (6 pages).
Final Office Action for U.S. Appl. No. 12/622,351 dated Jun. 10, 2011, 12 pgs.
Applicant Initiated Interview Summary for U.S. Appl. No. 12/622,351 dated Nov. 10, 2011, 6 pgs.
Office Action for U.S. Appl. No. 12/622,351 dated Dec. 1, 2011, 16 pgs.
Interview Summary for U.S. Appl. No. 12/622,351 dated Jan. 24, 2012, 2pgs.
Amendment and Response for U.S. Appl. No. 12/622,351 dated Apr. 17, 2012, 11 pgs.
Office Action for U.S. Appl. No. 12/622,351 dated Jun. 27, 2012, 26 pgs.
Applicant Initiated Interview Request Form for U.S. Appl. No. 12/622,351 filed Nov. 2, 2012, 1 pg.
Applicant Initiated Interview Summary for U.S. Appl. No. 12/622,351 dated Nov. 8, 2012, 4 pgs.
Office Action Appendix for U.S. Appl. No. 12/622,351 dated Nov. 8, 2012, 3 pgs.
Amendment and response for U.S. Appl. No. 12/622,351 dated Dec. 26, 2012, 10 pgs.
Office Action for U.S. Appl. No. 12/622,351 dated Apr. 3, 2013, 29 pgs.
Applicant Initiated Interview Summary for U.S. Appl. No. 12/622,351 dated Jun. 11, 2013, 4 pgs.
Miscellaneous Communication for U.S. Appl. No. 12/622,351 dated Jun. 19, 2013, 4 pgs.
Office Action for U.S. Appl. No. 12/472,082 dated Jun. 2, 2011, 13 pgs.
Applicant Initiated Interview Summary for U.S. Appl. No. 12/472,082 dated Nov. 9, 2011, 5 pgs.
Office Action for U.S. Appl. No. 12/472,082 dated Dec. 2, 2011, 14 pgs.
Applicant Summary of Interview for U.S. Appl. No. 12/472,082 dated Jan. 24, 2012, 2 pgs.
Amendment for U.S. Appl. No. 12/472,082 dated Apr. 17, 2012, 10 pgs.
Final Office Action for U.S. Appl. No. 12/472,082 dated Sep. 13, 2012, 15 pgs.
Applicant Summary of Interview for U.S. Appl. No. 12/472,082 dated Feb. 11, 2013, 2 pgs.
Amendment for U.S. Appl. No. 12/472,082 dated Mar. 4, 2013, 9 pgs.
Applicant Initiated Interview Summary for U.S. Appl. No. 12/472,082 dated Mar. 5, 2013, 3 pgs.
Request for Continued Examination for U.S. Appl. No. 12/472,082 dated Mar. 12, 2013, 2 pgs.
Notice of Allowance for U.S. Appl. No. 12/472,082 dated Jun. 21, 2013, 14 pgs.
Search Report for EP12275202 dated Apr. 9, 2013, 8 pgs.
Final Office Action for U.S. Appl. No. 12/332,904 dated May 9, 2011, 11 pgs.
Notice of Appeal for for U.S. Appl. No. 12/332,904 dated Nov. 7, 2011, 1 pg.
Applicant Initiated Interview Summary for U.S. Appl. No. 12/332,904 dated Nov. 10, 2011, 5 pgs.
Office Action for U.S. Appl. No. 12/332,904 dated Nov. 18, 2011, 12 pgs.
Applicant Summary of Interview for U.S. Appl. No. 12/332,904 dated Jan. 24, 2012, 2 pgs.
Amendment for U.S. Appl. No. 12/332,904 dated Feb. 21, 2012, 9 pgs.
Final Office Action for U.S. Appl. No. 12/332,904 dated Jan. 3, 2013, 5 pgs.
RCE for U.S. Appl. No. 12/332,904 dated Jul. 2, 2013, 14 pgs.

* cited by examiner

APPARATUS AND METHODS FOR DEPLOYMENT OF A MODULAR STENT-GRAFT SYSTEM

CROSS-REFERENCE TO RELATED APPLICATIONS

This application is a continuation-in-part of U.S. Utility patent application Ser. No. 12/332,904, filed Dec. 11, 2008 and entitled "Low Profile Non-Symmetrical Stent," which claims priority to U.S. Provisional Patent Application Ser. No. 61/016,753, filed Dec. 26, 2007, each of the above-referenced disclosures are hereby incorporated by reference in their entireties.

BACKGROUND

The present invention relates generally to apparatus and methods for treating medical conditions, and more specifically, to stents and stent-grafts for use in body vessels to treat those medical conditions.

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Various existing self-expanding and balloon-expandable stent designs and configurations comprise generally symmetrical end regions including one or more apices formed of nitinol or another alloy wire formed into a ring. The apices commonly comprise relatively acute bends or present somewhat pointed surfaces, which may facilitate compression of the stent to a relatively small delivery profile due to the tight bend of the apices. Although having this advantage, in some situations, such relatively acute or pointed apices may be undesirable, in particular in vessel anatomies that are curved or tortuous such as, for example, the thoracic aorta.

The thoracic aorta presents a challenging anatomy for stent grafts used to treat thoracic aneurysms or dissections. The thoracic aorta comprises a curve known as the aortic arch, which extends between the ascending thoracic aorta (closet to the heart) and the descending thoracic aorta (which extends toward the abdominal aorta). Thoracic stent grafts are used to exclude thoracic aortic aneurysms. A stent graft's ability to conform to the tortuous anatomy of the aortic arch is a major concern. Current designs sometimes lack the desired sealing ability at the proximal end of the stent graft (closest to the heart). Also, current thoracic devices present a relatively large profile which, with some patients' anatomies may be problematic. Finally, many current stents have relatively acute points that may prevent them from being used in the aortic arch for fear of undesirable interaction with the artery wall after an extended amount of time in the patient.

Therefore, a generally nonsymmetrical stent having at least one relatively rounded apex that is less invasive in an expanded state than stents with more acute apices may alleviate the above problems, while providing an improved compliance to the aortic arch and increased radial force if used as a sealing and/or alignment stent, as well as a desirable ability to be crimped to a readily introducible diameter.

As one particular example, type-A thoracic aortic dissection (TAD-A) is a condition in which the intimal layer of the ascending thoracic aorta develops a tear, allowing blood to flow into the layers of the aortic wall, causing the development of a medial or subintimal hematoma. TAD-A is associated with a strikingly high mortality rate (about one-fourth to one-half of victims die within the first 24-48 hours). The only current treatment for TAD-A is open surgery, where the chest is opened, the aorta is clamped, and a vascular prosthesis is sewn in place. Operative mortality rate for this procedure may be around 10%. Endovascular treatment of TAD-B (which affects the descending thoracic aorta) has been effective in reducing short-term and longer term mortality. Therefore, it is desirable to provide an endovascular device configured to address the anatomic challenges of the thoracic aorta.

SUMMARY

The present invention provides apparatus and methods for deployment of a modular stent-graft system. In one embodiment, a prosthesis comprises a first tubular graft comprising a layer of graft material, at least one lumen extending longitudinally therein, and a first fenestration extending through the layer of graft material. A layer of fenestration covering material attaches to the layer of graft material. The layer of fenestration covering material is disposed in the lumen of the first tubular graft and partitions the first fenestration from the lumen of the first tubular graft. A first non-stented opening is disposed proximal to the first fenestration and communicates with the first fenestration between the layer of graft material and the fenestration covering material. In use, a second tubular graft sealably engages the first non-stented opening, and the second tubular graft further extends distally through the first fenestration and into a branch vessel.

In an alternative embodiment, a plurality of fenestrations extend through the layer of graft material. The layer of fenestration covering material is attached to the layer of graft material and partitions the plurality of fenestrations from the lumen of the first tubular graft. In use, the second tubular graft sealably engages the first non-stented opening, and the second tubular graft further extends distally through one of the plurality of fenestrations and into the branch vessel.

Advantageously, a physician may insert the second tubular graft in a proximal to distal direction through the first non-stented opening, through any of the desired plurality of fenestrations, and then into a branch vessel. The physician may select a desired fenestration based on the particular anatomy of a patient during use, e.g., the fenestration that best facilitates alignment or entry of the second tubular graft into a branch vessel. Regardless of the fenestration selected, a fluid seal is maintained at the point of the first non-stented opening by deployment and expansion of the second tubular graft into sealing engagement with the first non-stented opening.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following figures and description. The components in the figures are not necessarily drawn to scale, emphasis instead

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure. Reference throughout is made to proximal and distal apices, but those of skill in the art will appreciate that the proximal-distal orientation of stents of the present invention may be reversed without exceeding the scope of the present invention.

As shown in FIGS. 4-15, this novel stent is not symmetrical like many commercially available stents, in that the radius of curvature of the opposing proximal and distal apices is different between the top and bottom of the stent. The stents may be attached to either end of a stent graft to provide sealing and may be used internally or externally to the graft material to provide support to the graft.

The asymmetric stent may be configured such that, when used with a graft, it will provide a sufficiently strong radial force at the graft's end openings to hold the graft material open against the artery wall. Also, the stent is intended to be short in length so that the graft will include flexibility sufficient to accommodate a patient's anatomy. This combination of flexibility and strong radial force provides an improved seal between the graft and artery wall. In addition, enhanced flexibility is provided as well, particularly when one or more stents are used to provide short segments and better accommodate curves.

Figure 1:
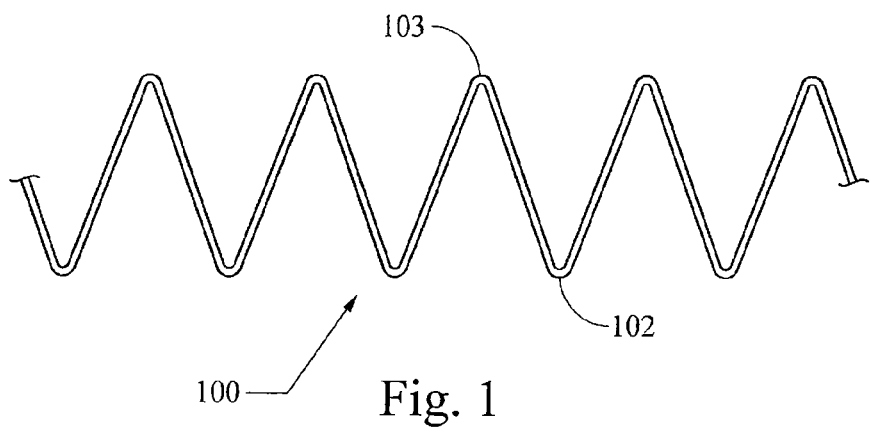
FIGS. 1-3 show different views of a symmetrical stent.
Figure 2:
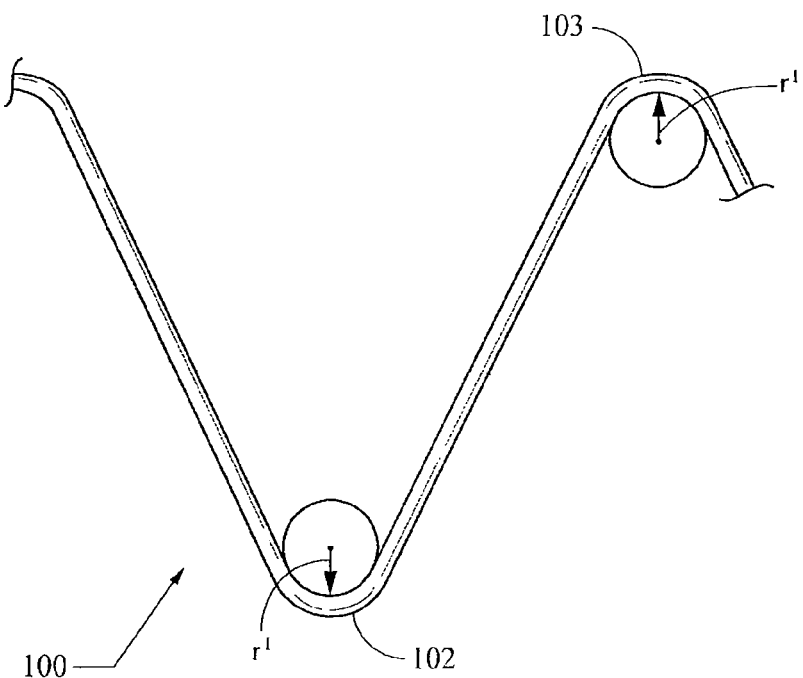
Figure 3:
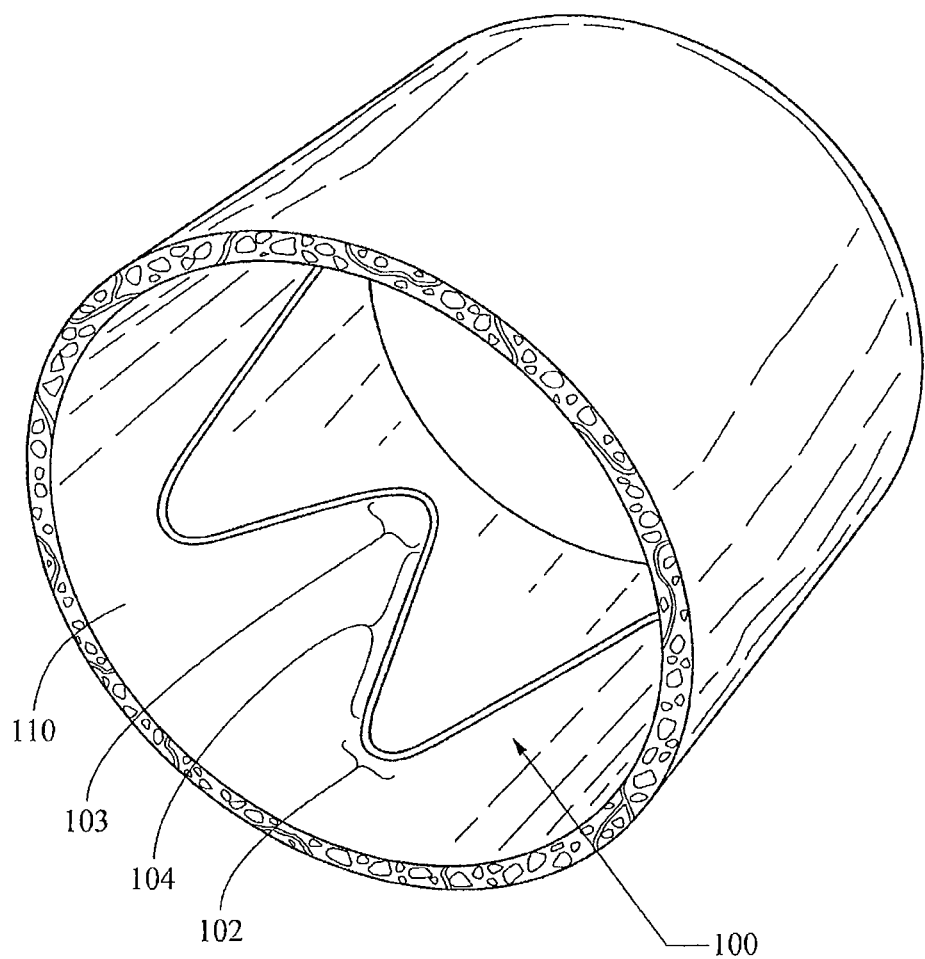

FIG. 1 shows a conventional stent 100, which has symmetrical apices 102, 103. Specifically, the proximal apices 102 and the distal apices 103 all have generally the same radii of curvature ($r^1$), which is illustrated in graphic form in FIG. 2. FIG. 3 is adapted from an FEA contour simulation and shows the stent 100 in a simulated artery 110, where the stent 100 is 20% oversized. The proximal and distal apices 102, 103 (circled) exert little or no pressure against the artery wall 110, while an intermediate region 107 exerts a higher pressure to provide—in one example—a total radial sealing force of 0.178 lbf. This configuration may be crimped to 18 Fr (e.g., for introduction via a catheter), with a maximum bend strain in the apices 102, 103 of about 5.8%. When using, for example, a typical NiTi wire for the stent, it is desirable not to exceed 10-12% strain to avoid increased risk of deforming the wire or adversely affecting its durability.

FIGS. 4-7 show a first example of a non-symmetrical stent 200, which is formed as a wire ring that has non-symmetrical proximal and distal generally curved apex portions (apices) 202, 203 separated from each other by intermediate generally straight portions. Specifically, the distal apices 203 all have generally the same radii of curvature ($r^d$) as each other, but the distal apices' radii of curvature are different from those of the proximal apices 202 ($r^p$). The distal apices 203 (which may be attached to and generally covered by graft material in a stent graft as described below with reference to FIGS. 14-15) are generally narrowly rounded in a manner not dissimilar from a traditional z-stent, but the proximal apices 202 are more broadly rounded. The difference in the proximal and distal apices 202, 203 is illustrated in graphic form in FIG. 5. In the illustrated example, the rounded proximal apices 202 have a radius of curvature of 6.0 mm, while the narrower distal apices 202 have a radius of curvature of 1.0 mm. In certain examples of non-symmetrical stents of the present invention, the radius of curvature of the rounded proximal apices (measured in the manner shown in FIG. 5) may be from about 4 mm to about 9 mm, and the radius of curvature of the narrower distal apices may be from about 0.5 mm to about 1.5 mm.

In these and other examples, the ratio of the proximal apices' radius of curvature to the distal apices' radius of curvature may be about 2.6:1 to about 18:1, and desirably may be about 6:1. The outer circumference of the stent 200 preferably is generally consistent such that, in this configuration, a solid outer face around the stent 200 would form a cylinder, although the stent will most preferably provide compliance with a surface less smooth than a cylinder.

Figure 6:
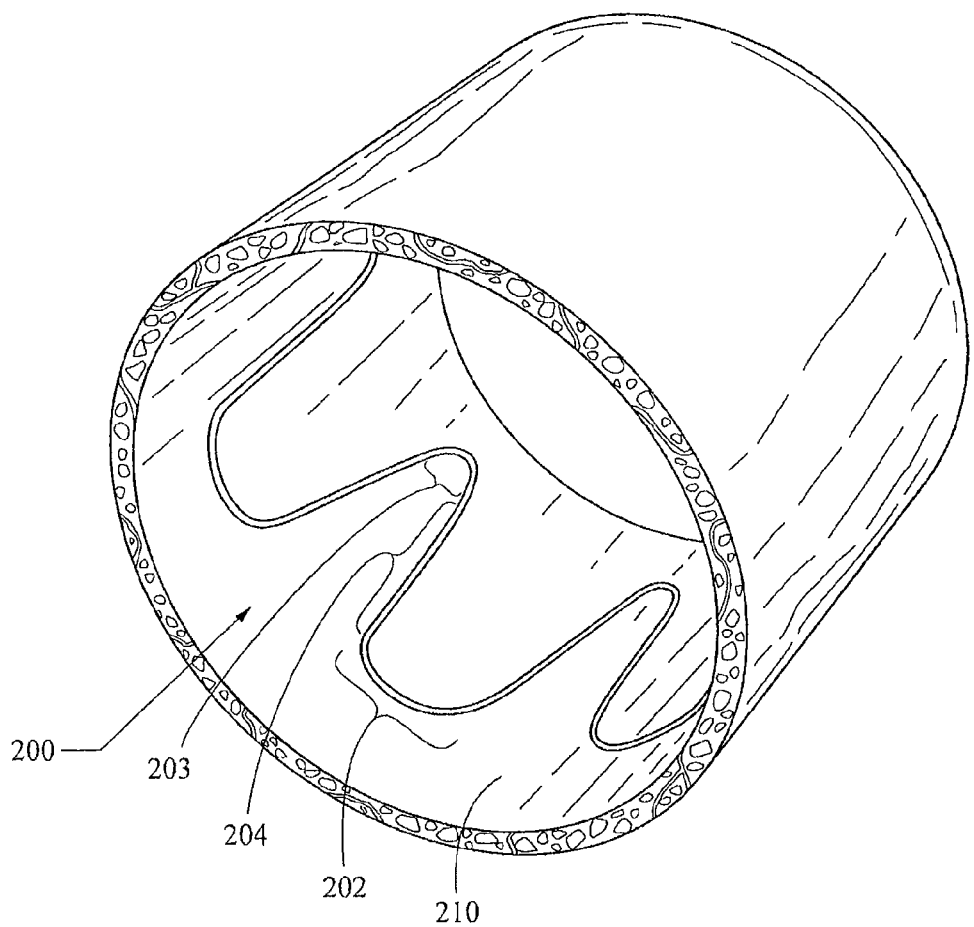
FIG. 6 shows the stent of FIG. 4 in a simulated artery.

FIG. 6 is adapted from an FEA contour simulation and shows the stent 200 in a simulated artery 210, where the stent 200 is 20% oversized. The proximal and distal apices 202, 203 (circled) exert little or no pressure against the artery wall 210, while an intermediate region 204 (boxed) exerts a greater pressure to provide—in the illustrated example—a total radial sealing force of about 0.160 lbf. This configuration may be crimped to 18 Fr, with a maximum bend strain in the apices 202, 203 of about 6.5%.

Figure 4:
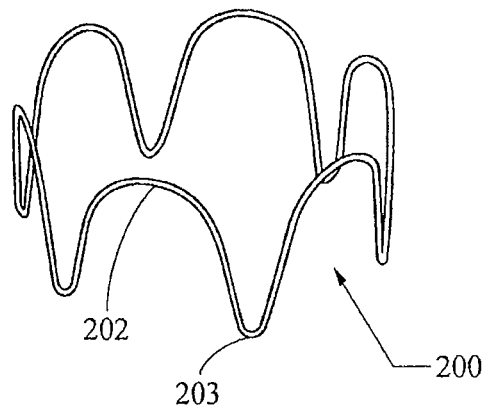
FIG. 4 depicts an example of an asymmetric stent.
Figure 5:
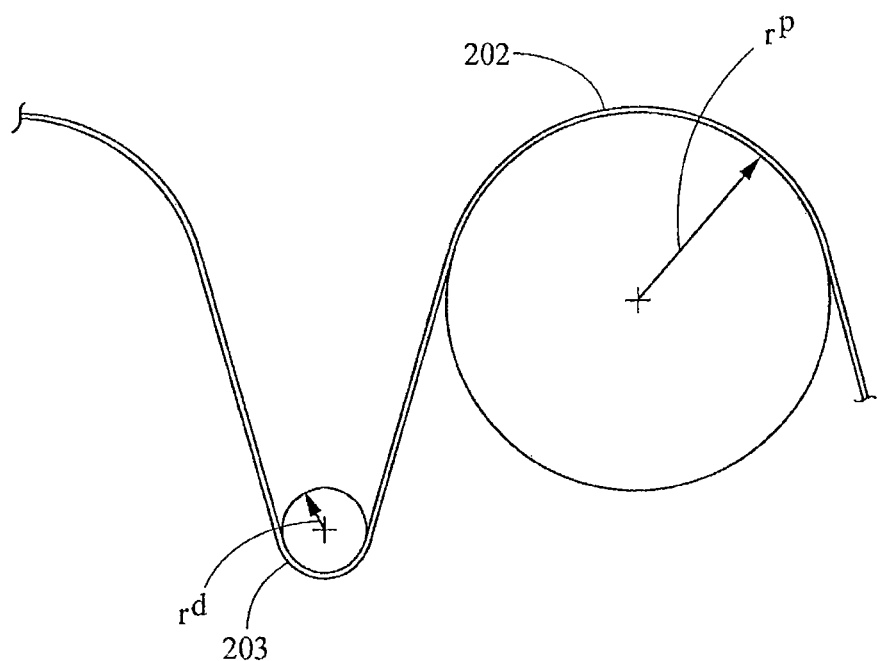
FIG. 5 diagrammatically illustrates the asymmetrical radii of curvature of the stent of FIG. 4.
Figure 7:
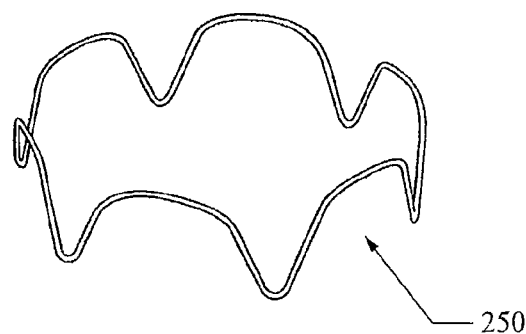
FIG. 7 depicts another example of an asymmetric stent.

FIG. 7 shows another non-symmetrical stent embodiment 250 that is very similar to the embodiment of FIGS. 4-6, but which has a shorter proximal-distal length. Each of the examples shown in FIGS. 4-7 may be manufactured in substantially the same manner as current z-stents, with a modification only of forming the proximal apices to include a greater radius of curvature than the distal apices.

Figure 8:
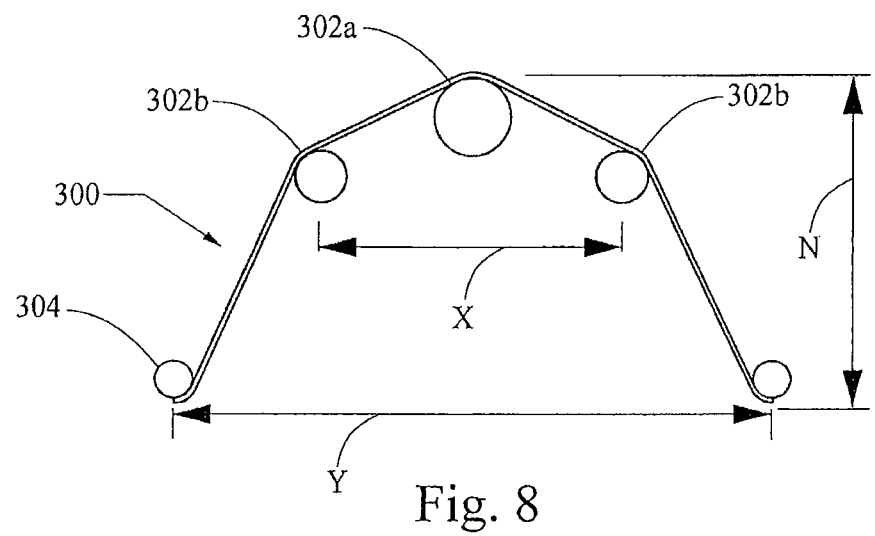
FIG. 8 diagrammatically illustrates the asymmetrical radii of curvature of yet another example of a stent.
Figure 9:
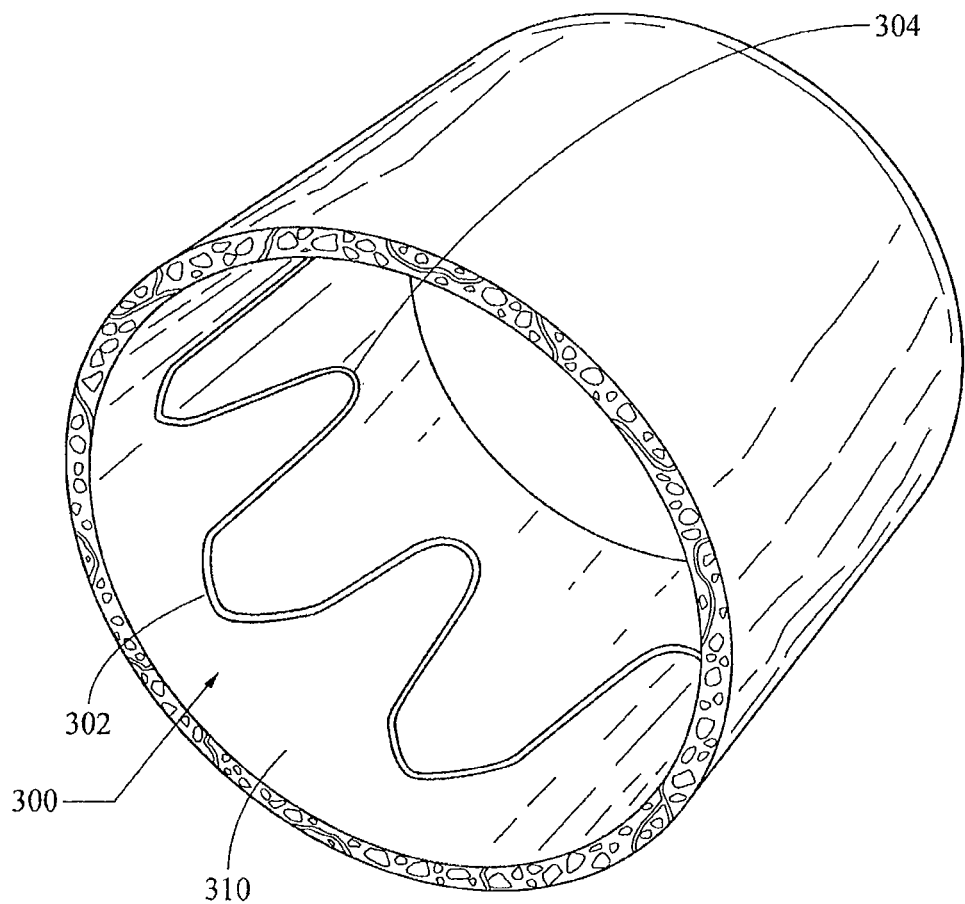
FIG. 9 shows the stent of FIG. 8 in a simulated artery.

FIGS. 8-9 illustrate another example of a non-symmetrical stent 300, which has a proximal "rounded roof shape" profile rather than the generally semicircular profile of the examples described above with reference to FIGS. 4-7. The profile of each proximal apex 302 includes a central fillet 302a and a pair of symmetrically opposed shoulder fillets 302b that may be generally equidistant from the central fillet 302a, or that may be disposed at varied distances therefrom. For the proximal apices of the stent 300, the central fillets 302a each have a radius of curvature of 1.0 mm, and the shoulder fillets 302b each have a fillet radius of curvature of 0.5 mm. The distal apices 304 have a radius of curvature of 1.0 mm. In another example having the rounded roof shape configuration (not shown), the central and shoulder fillets of proximal apices may each have the same radius of curvature such as, for example, 0.5 mm each, with distal apices also having a 0.5 mm radius of curvature. In other examples, the central and shoulder fillets 302a, 302b may each have a radius of curvature from about 0.5 mm to about 5 mm, and the distal apices may each have a radius of curvature of about 0.5 mm to about 1.5 mm. In another example having the rounded roof shape configuration (not shown), the ratio between the radii of curvature of the central and each shoulder fillet of the proximal apices may be about 3:1. FIG. 8 also shows three spans useful for describing desirable proportions in stent embodiments: "x" indicates the distance between the apical extremities of the shoulder fillets 302b, "y" indicates the distance between the tips of the distal apices 304, and "z" indicates the distance along a longitudinal axis between the tip of the distal apices 304 and the apical extremity of the proximal fillet 302a. Desirable embodiments may include an x:y ratio of about 1:3 to about 7:8 and a y:z ratio of about 1:1 to about 3:1. In yet another example (not shown), the filleted apices of this example may be combined with the generally semicircular apices of the example described with reference to FIGS. 4-7.

FIG. 9 is adapted from an FEA contour simulation and shows the stent 300 in a simulated artery 310, where the stent 300 is 20% oversized. The proximal and distal apices 302, 304 exert little or no pressure against the artery wall 310, while an intermediate region exerts a greater pressure to provide—in the illustrated example—a total radial sealing force of about 0.420 lbf. This configuration may be crimped to 18 Fr, with maximum bend strains in the apices that may be less than about 9% and preferably are less than about 10-12%. The greater radial sealing force of this example may provide advantages for stent placement and retention in certain circumstances as compared to existing z-stents.

Figure 10:
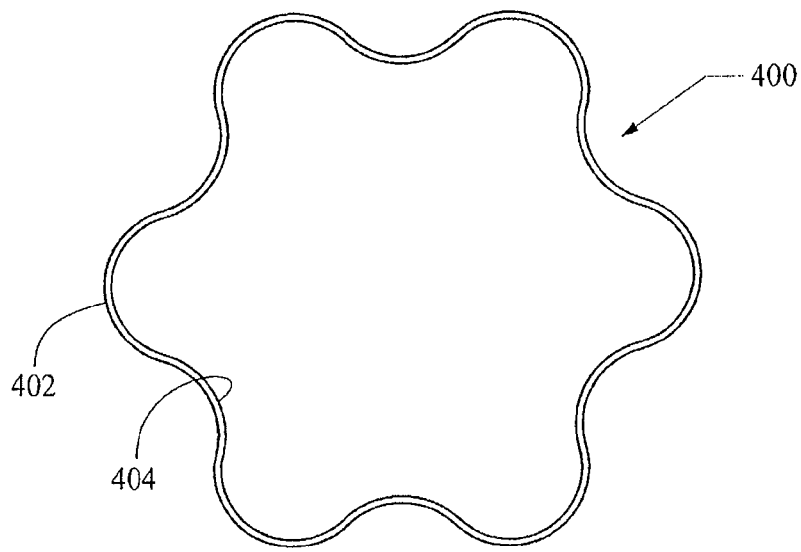
FIG. 10 shows an end view of still another example of an asymmetric stent.
Figure 11:
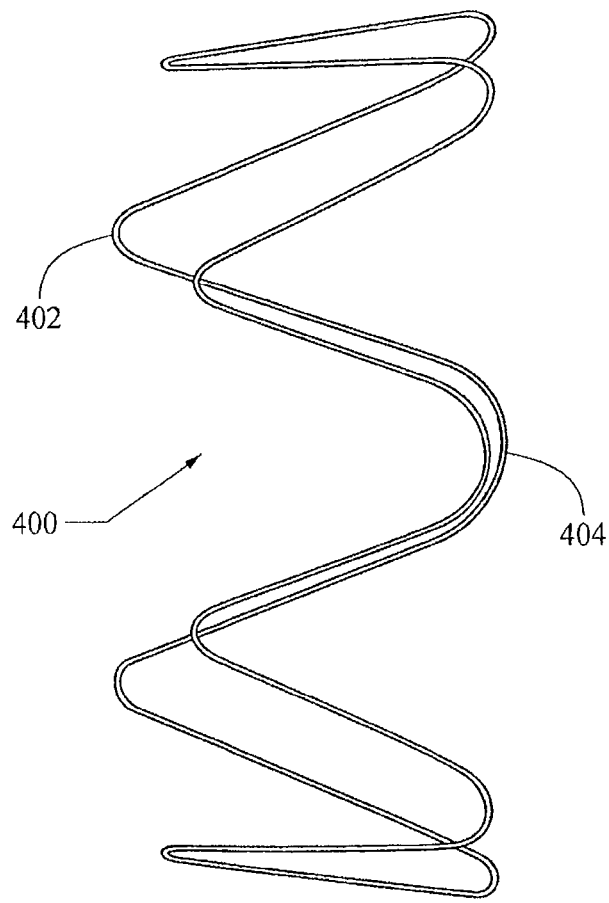
FIG. 11 shows a side view of the stent of FIG. 10.
Figure 12:
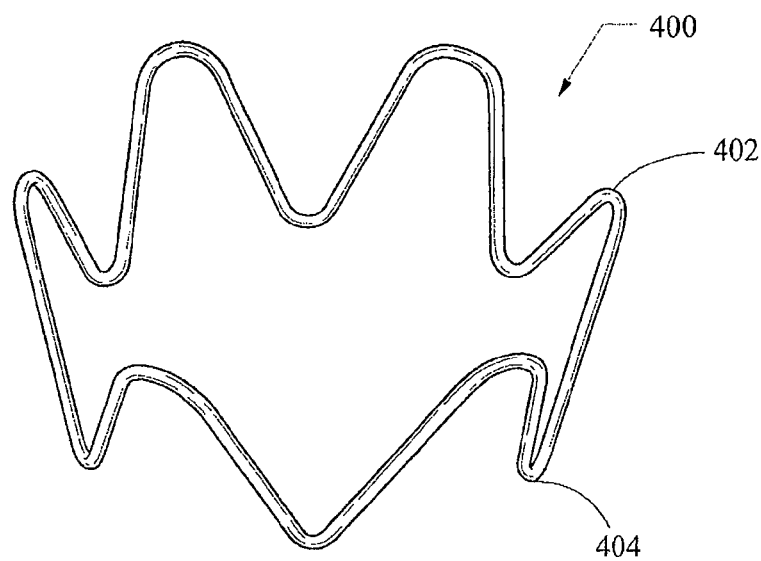
FIG. 12 is a top perspective view of the stent of FIG. 10.

FIGS. 10-13 illustrate another example of a non-symmetrical stent 400, which has an expanded "flower configuration" as shown in FIG. 10. Specifically, when the stent 400 is in an expanded configuration, the circumference around the proximal more-rounded apices 402 is greater than the circumference around the distal less-rounded apices 404, which is shown most clearly in FIGS. 11-14. In this configuration a solid outer face around an expanded stent 400 would form a frustum of a cone. This configuration may be manufactured in the same manner as the examples described above with reference to FIGS. 4-7 (i.e., producing a stent with a generally uniform outer circumference), with an added step that may include drawing the distal apices 404 into a smaller circumference upon suturing them to a smaller diameter graft material. Alternatively, or in addition, the stent 400 may be heat-set to impose the desired shape.

Figure 13:
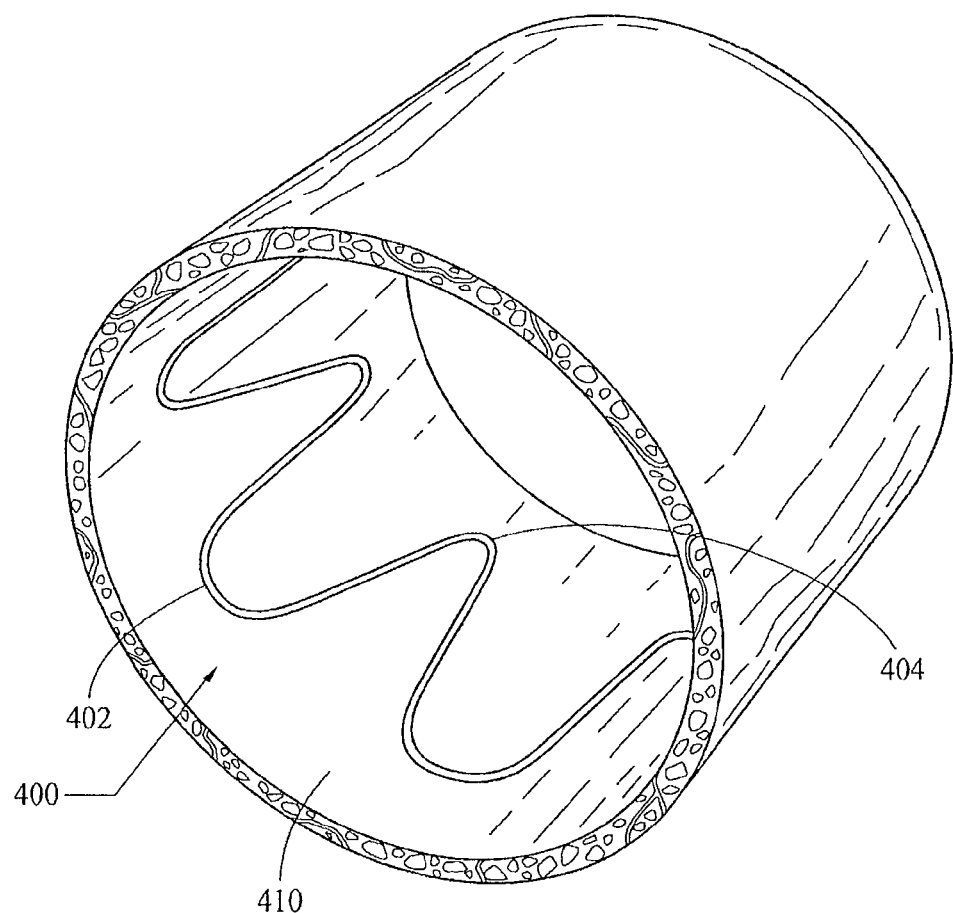
FIG. 13 shows the stent of FIG. 10 in a simulated artery.

FIG. 13 is adapted from an FEA contour simulation and shows the stent 400 in a simulated artery 410, where the stent 400 is 20% oversized. Surprisingly, the contour of pressure distribution along proximal and distal apices 402, 404 as well as an intermediate region is generally uniform throughout the stent circumference. The illustrated configuration provides a total radial sealing force of about 0.187 lbf. This property of generally uniform pressure distribution may provide advantages in certain applications of providing a seal and/or presenting less abrasion of a vessel wall through graft material as compared to stents with less uniform pressure distribution.

Figure 14:
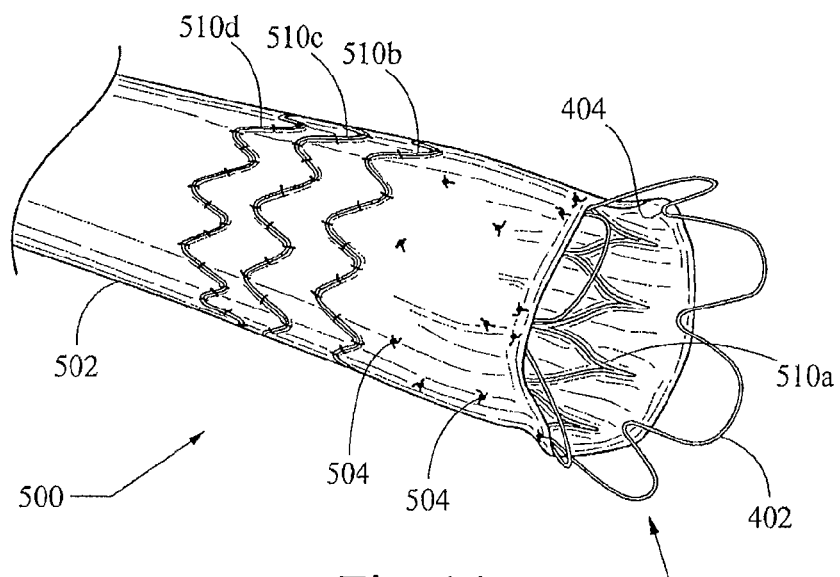
FIG. 14 is a partial perspective of a stent-graft incorporating the stent of FIG. 10.
Figure 15:
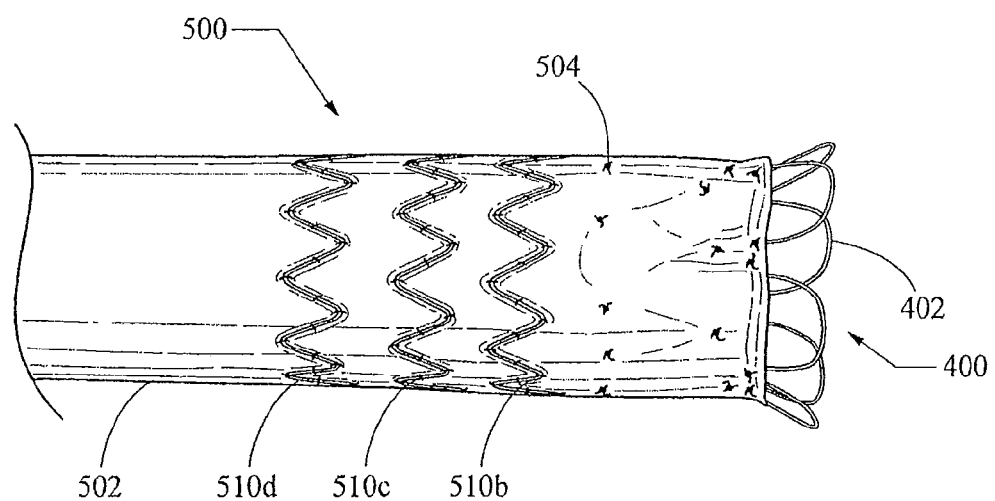
FIG. 15 illustrates a side view of the stent-graft of FIG. 14.

FIGS. 14-15 show two different views of a stent graft 500 using a stent example 400 of the present invention described above with reference to FIGS. 10-13. The stent graft 500 is shown in an expanded state and may be configured for use in treating a thoracic aortic aneurysm. The stent 400 is disposed at the proximal end of a generally cylindrical graft sleeve 502, to which its distal apices 404 are secured by sutures 504. The stent graft 500 also includes a series of z-stents 510a-d disposed distally from the stent 400. The first z-stent 510a is attached to the inner circumference of the graft 502, and the other z-stents 510b-510d are attached to the outer diameter of the graft 502. The proximal end of the stent 400 extends beyond the proximal end of the graft in a manner that may facilitate anchoring the graft in a vessel of a patient (e.g., a blood vessel).

The rounded points on the stent may protrude from the graft material only a small amount as is shown in FIGS. 14-15. In this example, only a small portion of the bare wire will be exposed to the artery wall. These unique (larger radii) rounded points are far less likely to perforate the artery wall than sharper points of a different stent configuration. Advantageously, this asymmetric stent design will maximize the efficacy of the seal while preserving the condition of the artery wall. Specifically, the narrower stent apices will provide for desirable radial expansion/sealing force, and the broader rounded apices will provide for a desirably atraumatic contact with an artery wall.

Figure 16:
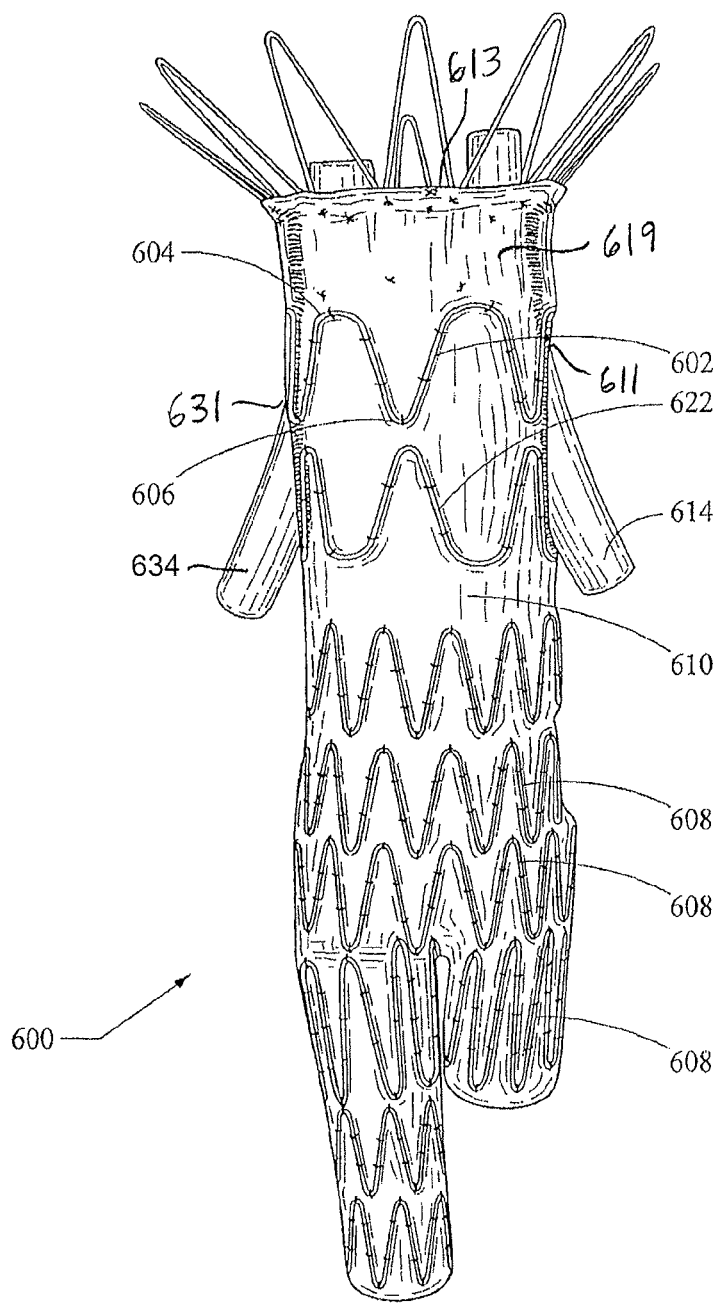
FIGS. 16-18 show a first embodiment of a modular stent-graft system.
Figure 17:
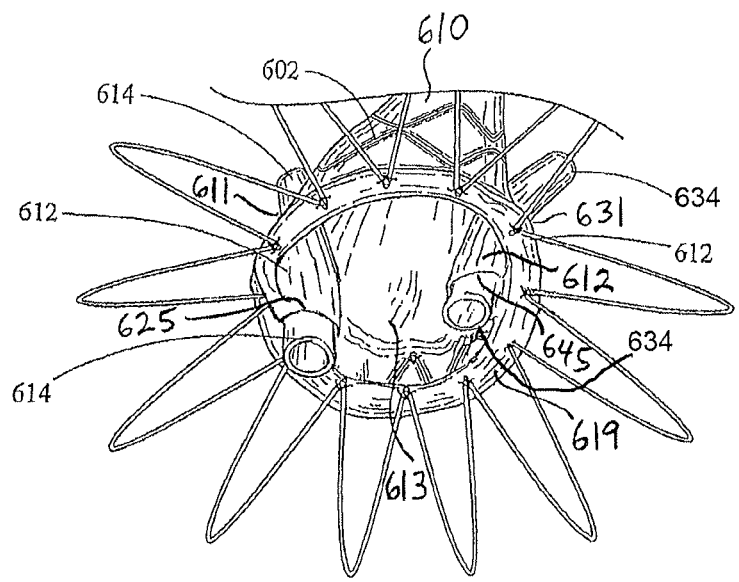
Figure 18:
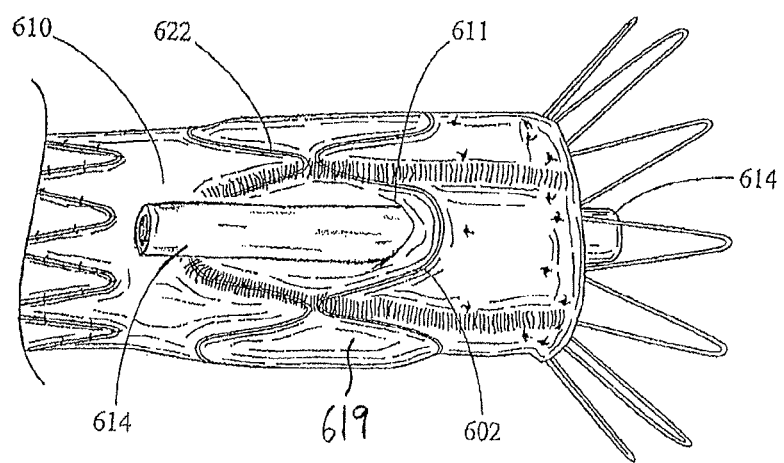

FIGS. 16-18 show a modular stent-graft embodiment 600 that includes a first tubular graft 610 comprising a layer of graft material 619 and at least one lumen 613 extending longitudinally therein. A first fenestration 611 extends through the layer of graft material 619, as best seen in FIG. 18.

A layer of fenestration covering material 612 is attached to the layer of graft material 619, disposed in the lumen 613 of the first tubular graft 610, and partitions the first fenestration 611 from the lumen 613, as shown in FIG. 17. Further, a first non-stented opening 625 is disposed proximal to the first fenestration 611 and communicates with the first fenestration 611 between the layer of graft material 619 and the fenestration covering material 612.

In use, a second tubular graft 614, comprising proximal and distal ends and a lumen extending longitudinally therebetween, sealably engages the first non-stented opening 625, as best seen in FIG. 17, and the second tubular graft 614 further extends through the first fenestration 611, as best seen in FIG. 18. Therefore, the second tubular graft 614 forms a secure fluid conduit to channel blood into a branch vessel, such as the renal arteries, when the first tubular graft 610 is positioned within a host vessel such as the aorta.

As shown in FIG. 17, the first non-stented opening 625 comprises a perimeter formed by a combination of the layer of graft material 619 and the fenestration covering material 612. In one embodiment, less than half of the perimeter of the first non-stented opening 625 is formed by the layer of graft material 619, whereas in another embodiment less than half of the perimeter of the first non-stented opening 625 is formed by the fenestration covering material 612.

Further, the prosthesis may comprise a second fenestration 631 and a second non-stented opening 645 disposed proximal to the second fenestration 631, as best seen in FIG. 17. The same or a separate fenestration covering material 612 further partitions the second fenestration 631 from the lumen 613 of the first tubular graft 610, such that the second non-stented opening 645 communicates with the second fenestration 631 between the layer of graft material 619 and the fenestration covering material 612. A third tubular graft 634, comprising proximal and distal ends and a lumen extending longitudinally therebetween, sealably engages the second non-stented opening 645, as best seen in FIG. 17, and the third tubular graft 634 further extends through the second fenestration 631, as best seen in FIG. 16.

In one embodiment, the first and/or second non-stented openings 625 and 645 are disposed about even with a proximal end of the first tubular graft 610. Further, the first and second non-stented openings 625 and 645 may be positioned between about 130 to about 230 degrees apart from one another around a circumference of the layer of graft material 619, and more preferably about 180 degrees apart, as depicted in FIG. 17. The first and second non-stented openings 625 and 645 may comprise a substantially circular or elliptical shape, as depicted in FIG. 17.

While the second and third tubular grafts 614 and 634 are shown as generic tubes, the second and/or third tubular grafts 614 and 634 may comprise first and second stents disposed at the proximal and distal ends, respectively. The first stents disposed at the proximal ends may expand into engagement with the non-stented openings 625 and 645, thereby providing a sealed conduit such that blood only flows distally into the main lumen 613 or one of the second and third tubular grafts 614 and 634. The second stents disposed at the distal ends of the second and third tubular grafts 614 and 634 may anchor into engagement with a branch vessel, such as the renal arteries.

Further, in the embodiment of FIGS. 16-18, the first tubular graft 610 comprises at least one non-symmetrical stent 602 having more broadly rounded proximal apices 604 and more narrowly rounded distal apices 606. The stent 602 is attached by sutures to the inner surface or outer surface of a generally columnar graft 610, which includes other stents 608. In this embodiment, the second and third tubular grafts 614 and 634 will advantageously be disposed generally transversely through the inner radius of the more broadly rounded proximal apices 604 of the stent 602, which provides atraumatic columnar support for the graft 610 as well as an anchor for the tubular structures 614. The stent-graft 600 may be particularly useful for treatment of an abdominal aortic aneurysm (AAA) that is immediately adjacent to, or that goes across, the renal arteries such that it has a short neck and lacks a contact area that is sufficient to create an effective proximal seal and avoid the proximal Type I endoleaks that may occur with some currently-available AAA stent-grafts. Those of skill in the art will appreciate that the stent-graft 600 will allow general occlusion of the AAA, while providing patent passage through the descending aorta and from the aorta to the renal arteries. Specifically, a stent-graft configured in the manner of the stent-graft embodiment 600, which includes a modular design that may include branch stents and/or stent-grafts, will allow a seal to be formed above the renal arteries and below the celiac and superior mesenteric arteries. Also, as shown in FIG. 16, a second non-symmetrical stent 622 may be placed adjacent the first non-symmetrical stent 602 in an opposite orientation that will provide additional atraumatic support for the branching second and third tubular grafts 614 and 634.

Figure 19:
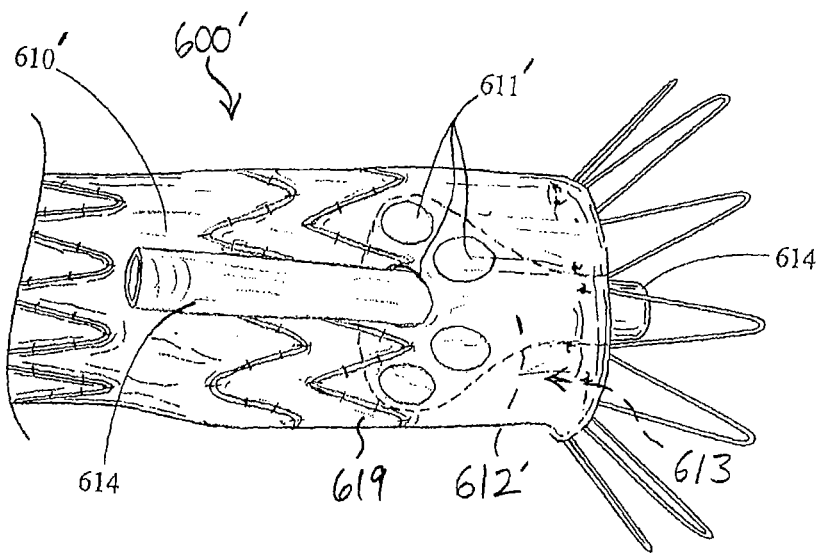
FIG. 19 shows an alternative embodiment of a modular stent-graft system.

Referring to FIG. 19, an alternative modular stent-graft embodiment 600' is similar to the stent-graft embodiment 600 described above, with the main exception that a plurality of fenestrations 611' extend through the layer of graft material 619 in the first tubular graft 610'. A layer of fenestration covering material 612' is attached to the layer of graft material 619, wherein the layer of fenestration covering material 612' is disposed in the lumen 613 of the first tubular graft 610' and partitions the plurality of fenestrations 611' from the lumen 613 of the first tubular graft 610'.

As in the embodiment of FIGS. 16-18, second and/or third tubular grafts 614 and 634 may be used in conjunction with the first tubular graft 610' to convey blood flow to one or more branch vessels. In use, a proximal portion of the second tubular graft 614 sealably engages the first non-stented opening 625 (see FIG. 17), and the second tubular graft 614 further extends distally through one of the plurality of fenestrations 611'. The layer of fenestration covering material 612' preferably comprises a distal segment that is flared relative to a proximal segment, as shown in FIG. 19, to thereby generally surround all of the fenestrations 611'.

Advantageously, in this manner, a physician may insert the second and/or third tubular grafts 614 and 634 in a proximal to distal direction through the non-stented openings 625 and 645, through any of the desired plurality of fenestrations 611', and then into a branch vessel. The physician may select a desired fenestration 611' based on the particular anatomy of a patient during use, e.g., the fenestration 611' that best facilitates alignment or entry of the second and/or third tubular grafts 614 and 634 into a branch vessel. Regardless of the fenestration 611' selected, a fluid seal is maintained at the point of the non-stented openings 625 and 645 by deployment and expansion of the second and third tubular grafts 614 and 634 into sealing engagement with the non-stented openings 625 and 645.

Figure 20:
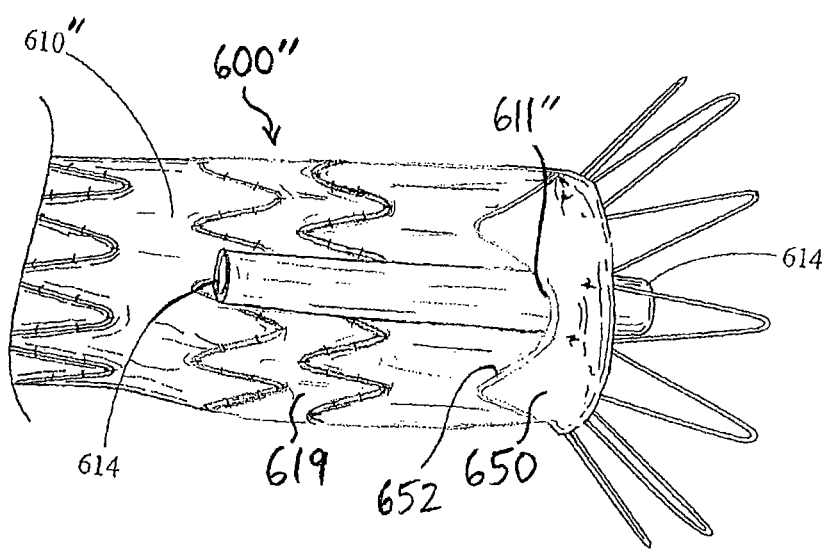
FIG. 20 shows a further alternative embodiment of a modular stent-graft system.

Referring to FIG. 20, an alternative stent-graft embodiment 600" is similar to the stent-graft embodiments 600 and 600' described above, with the main exception that an open fenestrations 611" extends through a folded back portion 650 of the layer of graft material 619 of a tubular graft 610". A stent 652 may be disposed in the folded back portion 650 to facilitate radial expansion of the tubular graft 610", whereby the open fenestrations 611" may be positioned adjacent to a strut of the stent 652, as shown in FIG. 20. As in the embodiment of FIGS. 16-19, second and/or third tubular grafts 614 and 634 may be used in conjunction with the first tubular graft 610 to convey blood flow to one or more branch vessels. In use, a proximal portion of the second tubular graft 614 sealably engages the first non-stented opening 625 (see FIG. 17), and the second tubular graft 614 further extends distally through the open fenestration 611". Advantageously, in this manner, a physician may insert the second and/or third tubular grafts 614 and 634 in a proximal to distal direction through the non-stented openings 625 and 645, through the open fenestration 611", and then into a branch vessel. The open fenestration 611" facilitates alignment or entry of the second and/or third tubular grafts 614 and 634 into a branch vessel.

Figure 21:
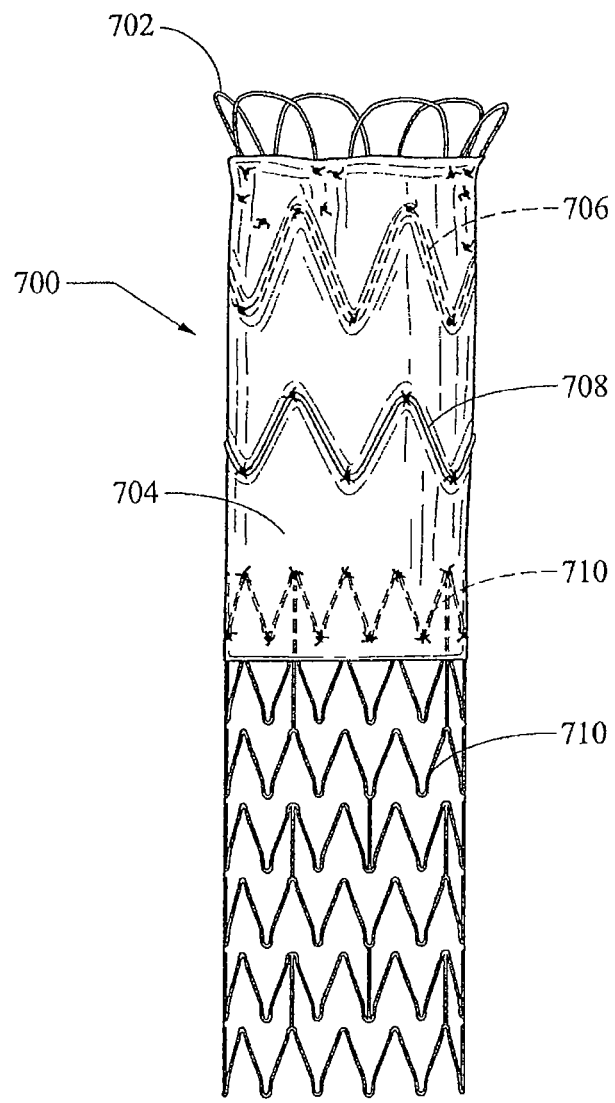
FIG. 21 is a side view of a stent-graft device configured for endovascular treatment of a thoracic aorta dissection.

FIG. 21 shows a stent-graft device 700 configured for endovascular treatment of a thoracic aorta dissection. The device 700 includes a non-symmetrical alignment stent 702 attached to a first end of a tubular graft material 704. A sealing stent 706 is attached in the central lumenal graft space proximate the alignment stent 702. The sealing stent 706 preferably is configured with a high radial force to promote efficacious sealing of the graft material 704 against a vessel wall. A body stent 708 configured here as a z-stent is disposed on the exterior of the graft material 704 and preferably is configured to provide longitudinal and circumferential stability/columnar support for the graft material of the device 700, such that it will conform to the vasculature and resist buckling when deployed in torturous anatomy such as the ascending thoracic aorta. A bare cannula stent 710 (such as, for example, a cut nitinol stent) is attached in the tubular graft material 704 at the opposite end from the alignment stent 702. This cannula stent 710 preferably is a conformable kink-resistant stent that provides distal sealing and migration-resistance. In a deployment of the device 700 to treat an aortic dissection, the alignment stent 702 preferably will be disposed proximal (nearer the heart) relative to the vessel tear, with the graft material traversing the tear in a manner generally sealing it from blood flow. And, the distal cannula stent 710 will help conform to the vasculature and retain a seal for treatment of the dissection. One or more of the sealing stent 706, body stent 708, and bare stent 710 may include one or more barbed projections configured to help anchor the device 700.

Stent examples of the present invention may be constructed of NiTi alloys or other materials presently known or yet to be developed, all within the scope of the present invention. The stents preferably are made from Nitinol wire and will therefore be MRI compatible. In another preferable embodiment, a stent may be made from a laser-cut Nitinol cannula, effectively rendering it a seamless or nearly-seamless wire-like construction. Nitinol's superelastic properties will facilitate the stents ability to be crimped down into a low profile delivery system.

While various embodiments of the invention have been described, it will be apparent to those of ordinary skill in the art that many more embodiments and implementations are possible within the scope of the invention. Accordingly, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A prosthesis comprising:
    a first tubular graft comprising a layer of graft material, at least one lumen extending longitudinally therein, and a plurality of fenestrations extending through the layer of graft material;
    a layer of fenestration covering material attached to the layer of graft material, wherein the layer of fenestration covering material is disposed in the lumen of the first tubular graft and partitions the plurality of fenestrations from the lumen of the first tubular graft;
    a first non-stented opening disposed proximal to the plurality of fenestrations and communicating with at least one of the plurality of fenestrations between the layer of graft material and the fenestration covering material; and
    a second tubular graft comprising a proximal end and a distal end and a lumen extending longitudinally therebetween,
    where the second tubular graft sealably engages the first non-stented opening, and the second tubular graft further extends distally through one of the plurality of fenestrations and is configured to extend into a branch vessel.

2. The prosthesis of claim 1, where the layer of fenestration covering material comprises a distal segment that is flared relative to a proximal segment.

3. The prosthesis of claim 1, where the first non-stented opening is disposed about even with a proximal end of the first tubular graft.

4. The prosthesis of claim 1, where the first non-stented opening comprises a perimeter formed by a combination of the layer of graft material and the fenestration covering material, wherein less than half of the perimeter of the first non-stented opening is formed by the layer of graft material.

5. The prosthesis of claim 1, where the first non-stented opening comprises a perimeter formed by a combination of the layer of graft material and the fenestration covering material, wherein less than half of the perimeter of the first non-stented opening is formed by the fenestration covering material.

6. A prosthesis comprising:
    a first tubular graft comprising a layer of graft material, at least one lumen extending longitudinally therein, and a plurality of fenestrations extending through the layer of graft material;
    a layer of fenestration covering material attached to the layer of graft material, wherein the layer of fenestration covering material is disposed in the lumen of the first tubular graft and partitions the plurality of fenestrations from the lumen of the first tubular graft;
    wherein the layer of fenestration covering material comprises a distal segment that is flared relative to a proximal segment and wherein the flared distal segment generally surrounds the plurality of fenestrations extending through the layer of the graft material;
    a first non-stented opening disposed proximal to the plurality of fenestrations and communicating with at least one of the plurality of fenestrations between the layer of graft material and the fenestration covering material; and
    a second tubular graft comprising a proximal end and a distal end and a lumen extending longitudinally therebetween,
    where the second tubular graft sealably engages the first non-stented opening, and the second tubular graft further extends distally through one of the plurality of fenestrations and is configured to extend into a branch vessel.

\* \* \* \* \*